United States Patent
Baldassari et al.

(10) Patent No.: US 9,440,894 B2
(45) Date of Patent: Sep. 13, 2016

(54) INTEGRATION OF RESIDUE HYDROCRACKING AND HYDROTREATING

(71) Applicant: Lummus Technology Inc., Bloomfield, NJ (US)

(72) Inventors: Mario C. Baldassari, Morris Plains, NJ (US); Ujjal K. Mukherjee, Montclair, NJ (US); Ann-Marie Olsen, Granite Springs, NY (US); Marvin I. Greene, Clifton, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 282 days.

(21) Appl. No.: 14/197,969

(22) Filed: Mar. 5, 2014

(65) Prior Publication Data

US 2014/0262940 A1 Sep. 18, 2014

Related U.S. Application Data

(60) Provisional application No. 61/784,568, filed on Mar. 14, 2013.

(51) Int. Cl.
*C10G 65/10* (2006.01)
*C10G 65/12* (2006.01)
(Continued)

(52) U.S. Cl.
CPC ............ *C07C 4/06* (2013.01); *C10G 65/12* (2013.01); *C10G 2300/107* (2013.01); *C10G 2300/1077* (2013.01); *C10G 2300/202* (2013.01); *C10G 2300/4081* (2013.01)

(58) Field of Classification Search
CPC ...... C10G 65/00; C10G 65/10; C10G 65/12; C07C 4/00; C07C 4/06; C07C 4/08; C07C 4/10; C07C 4/18
See application file for complete search history.

(56) References Cited

U.S. PATENT DOCUMENTS 4,789,462 A 12/1988 Byrne et al.
4,976,848 A 12/1990 Johnson
(Continued)

FOREIGN PATENT DOCUMENTS

CN 102037101 A 4/2011
EP 1392800 B1 3/2004
(Continued)

OTHER PUBLICATIONS

Office Action issued in corresponding Taiwanese Application No. 103108375 with partial translation dated Feb. 10, 2015 (10 pages).
(Continued)

*Primary Examiner* — Brian McCaig
(74) *Attorney, Agent, or Firm* — Osha • Liang LLP (57) ABSTRACT

A process for upgrading residuum hydrocarbons is disclosed. The process may include: contacting a residuum hydrocarbon fraction and hydrogen with a first hydroconversion catalyst in a first ebullated bed hydroconversion reactor system; recovering a first effluent from the first ebullated bed hydroconversion reactor system; solvent deasphalting a vacuum residuum fraction to produce a deasphalted oil fraction and an asphalt fraction; contacting the deasphalted oil fraction and hydrogen with a second hydroconversion catalyst in a second hydroconversion reactor system; recovering a second effluent from the second hydroconversion reactor system; and fractionating the first effluent from the first ebullated bed hydroconversion reactor system and the second effluent from the second hydroconversion reactor system to recover one or more hydrocarbon fractions and the vacuum residuum fraction in a common fractionation system.

16 Claims, 4 Drawing Sheets

(51) Int. Cl.
*C07C 4/06* (2006.01)
*C10G 65/00* (2006.01)

(56) References Cited

U.S. PATENT DOCUMENTS

| | | | |
|---|---|---|---|
| 4,990,243 | A | 2/1991 | Winslow et al. |
| 5,017,805 | A | 5/1991 | Kase |
| 5,177,047 | A | 1/1993 | Threlkel |
| 5,215,955 | A | 6/1993 | Threlkel |
| 5,472,928 | A | 12/1995 | Scheuerman et al. |
| 5,494,570 | A | 2/1996 | Nongbri et al. |
| 5,914,010 | A | 6/1999 | Hood et al. |
| 5,932,090 | A | 8/1999 | Marchionna et al. |
| 5,980,730 | A | 11/1999 | Morel et al. |
| 5,980,732 | A | 11/1999 | Gillis |
| 6,007,703 | A | 12/1999 | Morel et al. |
| 6,017,441 | A | 1/2000 | Morel et al. |
| 6,117,306 | A | 9/2000 | Morel et al. |
| 6,156,695 | A | 12/2000 | Soled et al. |
| 6,162,350 | A | 12/2000 | Soled et al. |
| 6,280,606 | B1 | 8/2001 | Morel et al. |
| 6,447,671 | B1 | 9/2002 | Morel et al. |
| 7,300,900 | B2 | 11/2007 | Benazzi et al. |
| 7,476,309 | B2 | 1/2009 | Abe et al. |
| 7,566,394 | B2 | 7/2009 | Koseoglu |
| 7,594,990 | B2 | 9/2009 | Satchell, Jr. |
| 7,686,943 | B2 | 3/2010 | Soled et al. |
| 7,691,256 | B2 | 4/2010 | Montanari et al. |
| 7,938,952 | B2 | 5/2011 | Colyar et al. |
| 8,002,968 | B2 | 8/2011 | Flint et al. |
| 8,017,000 | B2 | 9/2011 | Montanari et al. |
| 8,034,230 | B2 | 10/2011 | Lenglet |
| 8,034,232 | B2 | 10/2011 | Lott et al. |
| 8,052,864 | B2 | 11/2011 | Eilers et al. |
| 8,062,505 | B2 | 11/2011 | Bhattacharyya et al. |
| 8,123,932 | B2 | 2/2012 | Montanari et al. |
| 8,123,933 | B2 | 2/2012 | Bhattacharyya et al. |
| 8,128,810 | B2 | 3/2012 | Bhattacharyya et al. |
| 8,133,446 | B2 | 3/2012 | McGehee et al. |
| 2004/0055934 | A1 | 3/2004 | Tromeur et al. |
| 2005/0006279 | A1 | 1/2005 | Gueret et al. |
| 2006/0272982 | A1 | 12/2006 | Montanari et al. |
| 2006/0283776 | A1 | 12/2006 | Iqbal et al. |
| 2007/0090018 | A1 | 4/2007 | Keusenkothen et al. |
| 2008/0085225 | A1 | 4/2008 | Bhan et al. |
| 2008/0116109 | A1 | 5/2008 | McCoy et al. |
| 2008/0223754 | A1 | 9/2008 | Subramanian et al. |
| 2009/0050524 | A1 | 2/2009 | Kim et al. |
| 2009/0107881 | A1* | 4/2009 | Lott et al. ............ 208/74 |
| 2009/0166250 | A1 | 7/2009 | Subramanian et al. |
| 2009/0166253 | A1 | 7/2009 | Subramanian et al. |
| 2009/0261016 | A1 | 10/2009 | Marchionna et al. |
| 2009/0288986 | A1 | 11/2009 | Colyar et al. |
| 2009/0301931 | A1 | 12/2009 | Koseoglu et al. |
| 2009/0314681 | A1 | 12/2009 | Marchionna et al. |
| 2010/0294701 | A1 | 11/2010 | Lott et al. |
| 2010/0320122 | A1 | 12/2010 | Baldassari et al. |
| 2011/0005976 | A1 | 1/2011 | Rispoli et al. |
| 2011/0017641 | A1 | 1/2011 | Gupta et al. |
| 2011/0036752 | A1 | 2/2011 | Gauthier et al. |
| 2011/0220546 | A1 | 9/2011 | Koseoglu et al. |
| 2011/0220553 | A1 | 9/2011 | Lott et al. |
| 2011/0253594 | A1 | 10/2011 | Marchionna et al. |
| 2012/0009094 | A1 | 1/2012 | Lott et al. |
| 2012/0061292 | A1 | 3/2012 | Sanchez et al. |
| 2012/0061293 | A1 | 3/2012 | Sanchez et al. |
| 2012/0103866 | A1 | 5/2012 | Biswas et al. |

FOREIGN PATENT DOCUMENTS

| | | |
|---|---|---|
| TW | 200932889 A | 8/2009 |
| WO | 2004056946 A2 | 7/2004 |
| WO | 2006006857 A1 | 1/2006 |
| WO | 2006079028 A1 | 7/2006 |
| WO | 2007001706 A2 | 1/2007 |
| WO | 2007047657 A1 | 4/2007 |
| WO | 2008014947 A1 | 2/2008 |
| WO | 2008045753 A2 | 4/2008 |
| WO | 2009003633 A1 | 1/2009 |
| WO | 2009003634 A1 | 1/2009 |
| WO | 2009111871 A1 | 9/2009 |

OTHER PUBLICATIONS

International Search Report issued in corresponding International Application No. PCT/US2014/020730 dated May 20, 2014 (6 pages).

Written Opinion issued in corresponding International Application No. PCT/US2014/020730 dated May 20, 2014 (8 pages).

* cited by examiner

INTEGRATION OF RESIDUE HYDROCRACKING AND HYDROTREATING

CROSS-REFERENCE TO RELATED APPLICATIONS

This application, pursuant to 35 U.S.C. §119(e), claims priority to U.S. Provisional Application Ser. No. 61/784,568, filed Mar. 14, 2013, which is herein incorporated by reference in its entirety.

FIELD OF THE DISCLOSURE

Embodiments disclosed herein relate generally to hydroconversion processes, including processes for hydrocracking residue and other heavy hydrocarbon fractions. More specifically, embodiments disclosed herein relate to hydrocracking of a residuum hydrocarbon feedstock, processing the resulting hydrocracked residuum hydrocarbon in a separate residue hydrotreating unit, and processing the product from the hydrotreating unit in a separate residue hydrocracking unit.

BACKGROUND

As the worldwide demand for gasoline and other light refinery products has steadily increased, there has been a significant trend toward conversion of higher boiling compounds to lower boiling ones. To meet the increasing demand for distillate fuels increased, refiners have investigated various reactors, such as hydrocracking reactors, residual desulfurization units (RDS), and solvent deasphalting (SDA) units, to convert Residuum, Vacuum Gas Oil (VGO) and other heavy petroleum feedstocks to jet and diesel fuels.

Catalysts have been developed that exhibited excellent distillate selectivity, reasonable conversion activity and stability for heavier feedstocks. The conversion rates attainable by the various processes are limited, however. For example, RDS units alone can produce a 1 wt % sulfur fuel from high sulfur residua, but conversions are generally limited to about 35% to 40%. Others have proposed to use SDA units to solvent deasphalt the residuum feed and process the deasphalted oil only in a Residuum Hydrocracking Unit (RHU). Also, others have processed the unconverted vacuum residuum from a RHU in an SDA unit and recycled the deasphalted oil (DAO) back to the front end of the RHU. Still others have proposed to process the SDA pitch directly in a RHU. Nonetheless, economic processes to achieve high hydrocarbon conversions and sulfur removal are desired.

SUMMARY

In one aspect, embodiments disclosed herein relate to a process for upgrading residuum hydrocarbons. The process may include the following steps: contacting a residuum hydrocarbon fraction and hydrogen with a first hydroconversion catalyst in a first ebullated bed hydroconversion reactor system; recovering a first effluent from the first ebullated bed hydroconversion reactor system; contacting the first effluent and hydrogen with a second hydroconversion catalyst in a second hydroconversion reactor system; recovering a second effluent from the second hydroconversion reactor system; contacting the second effluent and hydrogen with a third hydroconversion catalyst in a second ebullated bed hydroconversion reactor system; recovering a third effluent from the second ebullated bed hydroconversion reactor system; and fractionating the third effluent from the second ebullated bed hydroconversion reactor system to recover one or more hydrocarbon fractions.

In another aspect, embodiments disclosed herein relate to a system for upgrading residuum hydrocarbons. The system may include the following: a first ebullated bed hydroconversion reactor system for contacting a residuum hydrocarbon fraction and hydrogen with a first hydroconversion catalyst to produce a first effluent; a second hydroconversion reactor system for contacting the first effluent and hydrogen with a second hydroconversion catalyst to produce a second effluent; a second ebullated bed hydroconversion reactor system for contacting the second effluent and hydrogen with a third hydroconversion catalyst to produce a third effluent and a fractionation unit to fractionate the third effluent to recover one or more hydrocarbon fractions and the vacuum residuum fraction.

In another aspect, embodiments disclosed herein relate to a process for upgrading residuum hydrocarbons. The process may include the following steps: contacting a residuum hydrocarbon fraction and hydrogen with a first hydroconversion catalyst in a first ebullated bed hydroconversion reactor system; recovering a first effluent from the first ebullated bed hydroconversion reactor system; contacting the first effluent and hydrogen with a second hydroconversion catalyst in a second hydroconversion reactor system; recovering a second effluent from the second hydroconversion reactor system; contacting the second effluent and hydrogen with a third hydroconversion catalyst in a third hydroconversion reactor system; recovering a third effluent from the third hydroconversion reactor system; combining the second effluent and the third effluent to form a combined feed; feeding the combined feed to a separator to produce a vapor fraction and a liquid fraction; fractionating the liquid fraction to recover the vacuum residuum fraction in a first fractionation system; contacting the vapor fraction with a fourth hydroconversion catalyst in a fourth hydroconversion reactor system; recovering a fourth effluent from the third hydroconversion reactor system; fractionating the fourth effluent to recover one or more hydrocarbon fractions in a second fractionation system.

In another aspect, embodiments disclosed herein relate to a system for upgrading residuum hydrocarbons. The system may include the following: a first ebullated bed hydroconversion reactor system for contacting a residuum hydrocarbon fraction and hydrogen with a first hydroconversion catalyst to produce a first effluent; a second hydroconversion reactor system for contacting the first effluent and hydrogen with a second hydroconversion catalyst to produce a second effluent; a second ebullated bed hydroconversion reactor system for contacting the second effluent and hydrogen with a third hydroconversion catalyst to produce a third effluent; and a separator for separating a combined fraction of the second effluent and the third effluent to recover a liquid fraction and a vapor fraction; a fractionation unit to fractionate the liquid to recover the vacuum residuum fraction; a fourth hydroconversion reactor system for contacting the vapor fraction with a fourth hydroconversion catalyst to produce a fourth effluent; and a fractionation unit to fractionate the fourth effluent to recover one or more hydrocarbon fractions.

Other aspects and advantages will be apparent from the following description and the appended claims.

DETAILED DESCRIPTION

In one aspect, embodiments herein relate generally to hydroconversion processes, including processes for hydrocracking residue and other heavy hydrocarbon fractions. More specifically, embodiments disclosed herein relate to hydrocracking of a residuum hydrocarbon feedstock, hydrotreating the hydrocracked residuum hydrocarbon, processing the resulting hydrocracked product in a separate residue hydrocracking unit, and processing the pitch from the solvent deasphalting in a separate residue hydrocracking unit.

Hydroconversion processes disclosed herein may be used for reacting residuum hydrocarbon feedstocks at conditions of elevated temperatures and pressures in the presence of hydrogen and one or more hydroconversion catalyst to convert the feedstock to lower molecular weight products with reduced contaminant (such as sulfur and/or nitrogen) levels. Hydroconversion processes may include, for example, hydrogenation, desulfurization, denitrogenation, cracking, conversion, demetallization, and removal of metals, Conradson Carbon Residue (CCR) or asphaltenes removal, etc.

As used herein, residuum hydrocarbon fractions, or like terms referring to residuum hydrocarbons, are defined as a hydrocarbon fraction having boiling points or a boiling range above about 340° C. but could also include whole heavy crude processing. Residuum hydrocarbon feedstocks that may be used with processes disclosed herein may include various refinery and other hydrocarbon streams such as petroleum atmospheric or vacuum residua, deasphalted oils, deasphalter pitch, hydrocracked atmospheric tower or vacuum tower bottoms, straight run vacuum gas oils, hydrocracked vacuum gas oils, fluid catalytically cracked (FCC) slurry oils, vacuum gas oils from an ebullated bed hydrocracking process, shale-derived oils, coal-derived oils, tar sands bitumen, tall oils, bio-derived crude oils, black oils, as well as other similar hydrocarbon streams, or a combination of these, each of which may be straight run, process derived, hydrocracked, partially desulfurized, and/or partially demetallized streams. In some embodiments, residuum hydrocarbon fractions may include hydrocarbons having a normal boiling point of at least 480° C., at least 524° C., or at least 565° C.

Figure 1:
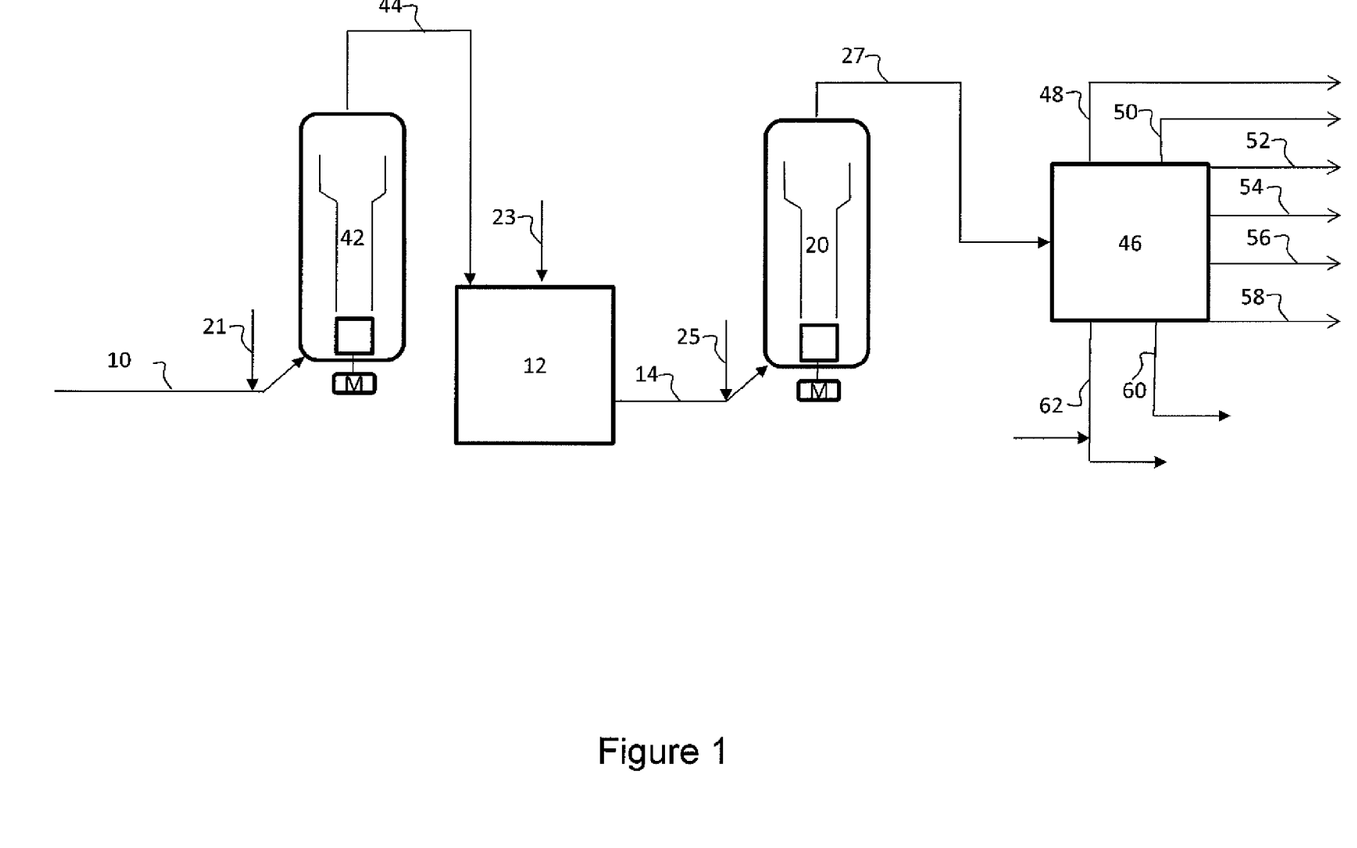
FIG. 1 is a simplified process flow diagram of a process for upgrading residuum hydrocarbon feedstocks according to embodiments disclosed herein.

Referring now to FIG. 1, a residuum hydrocarbon fraction (residuum) 10 and hydrogen 21 may be fed to an ebullated bed reactor system 42, which may include one or more ebullated bed reactors arranged in series or parallel, where the hydrocarbons and hydrogen are contacted with a hydroconversion catalyst to react at least a portion of the residuum with hydrogen to form lighter hydrocarbons, demetallize the metals contained in residuum, remove Conradson Carbon Residue, or otherwise convert the residuum to useful products. While shown as a single reactor train, the residuum hydrocarbon fraction (residuum) 10 may be processed in multiple parallel reactor trains. In some embodiments, the multiple reactor trains include sections common to the parallel trains, such as, but not limited to, fractionation, catalyst handling and recovery sections. The residuum hydrocarbon fraction (residuum) 10 feed to the ebullated bed reactor system 42 may be controlled via a surge drum operated with flow control.

In some embodiments, the residuum hydrocarbon fraction (residuum) 10 may be preheated. The preheating may be done via heat exchange with various streams (sidecuts) from either an atmospheric or a vacuum fractionation system. The residuum hydrocarbon fraction (residuum) 10 may also be heated using furnaces or any known feed/effluent heat exchange apparatus to provide the desired feed inlet temperature to the ebullated bed reactor 42.

In some embodiments, the hydrogen 21 may be a hydrogen-rich gas stream which may be a purified recycle stream with make-up hydrogen. The hydrogen 21 may be preheated before mixing with the residuum hydrocarbon fraction (residuum) 10.

Reactors in ebullated bed reactor 42 may be operated at temperatures in the range from about 380° C. to about 450° C., hydrogen partial pressures in the range from about 70 bara to about 170 bara, and liquid hourly space velocities (LHSV) in the range from about 0.2 $h^{-1}$ to about 2.0 $h^{-1}$. Within the ebullated bed reactors, the catalyst may be back mixed and maintained in random motion by the recirculation of the liquid product. This may be accomplished by first separating the recirculated oil from the gaseous products. The oil may then be recirculated by means of an external pump, or, as illustrated, by a pump having an impeller mounted in the bottom head of the reactor.

Target conversions in ebullated bed reactor system 42 may be in the range from about 30 wt % to about 50 wt %, depending upon the feedstock being processed. In any event, target conversions should be maintained below the level where sediment formation becomes excessive and thereby prevent continuity of operations. In addition to converting the residuum hydrocarbons to lighter hydrocarbons, sulfur removal may be in the range from about 40 wt % to about 65 wt %, metals removal may be in the range from about 50 wt % to 80 wt % and Conradson Carbon Residue (CCR) removal may be in the range from about 30 wt % to about 60 wt %.

Reactor severity may be defined as the catalyst average temperature in degrees Fahrenheit of the catalysts loaded in the one or more ebullated bed hydrocracking reactors multiplied by the average hydrogen partial pressure of the ebullated bed hydrocracking reactors in Bar absolute and divided by the LHSV in the ebullated bed hydrocracking reactors. The reactor severity of the ebullated bed reactor system 42 may be in the range from about 105,000° F.-Bara-Hr to about 446,000° F.-Bara-Hr.

Following conversion in ebullated bed reactor system 42, the partially converted hydrocarbons 44 may be may be treated with hydrogen 23 in a fixed bed reactor system 12, as illustrated. In some embodiments, the fixed bed reactor system 12 may include more than one reactor, either in parallel or series. In the fixed bed reactor system 12, the number of reactors used may depend on the charge rate, the overall target residue conversion level, and the level of conversion attained in ebullated bed reactor system 42, among other variables. In some embodiments, one or two reactors may be used in the fixed bed reactor system 12. In some embodiments, the hydrogen 23 may be a combination of cold and warm recycle gas from the fixed bed reactor system 12. In some embodiments, the fixed bed reactor system 12 includes a hydroprocessing catalyst. In other embodiments, the fixed bed reactor system 12 includes a hydrodemetallization catalyst.

Target conversions in the fixed bed reactor system 12 may be in the range from about 50 wt % to about 55 wt %, depending upon the feedstock being processed. In any event, target conversions should be maintained below the level where sediment formation becomes excessive and thereby prevent continuity of operations. In addition to converting the residuum hydrocarbons to lighter hydrocarbons, sulfur removal may be in the range from about 85 wt % to about 87 wt %, metals removal may be in the range from about 50 wt % to 80 wt % and Conradson Carbon Residue (CCR) removal may be in the range from about 65 wt % to about 70 wt %.

Following conversion in the fixed bed reactor system 12, the partially converted hydrocarbons may be recovered via flow line 14 as a mixed vapor/liquid effluent along with hydrogen 25 fed to a hydrocracking reactor system 20, which may include one or more hydro cracking reactors, arranged in series or parallel. In hydrocracking reactor system 20, the partially converted hydrocarbons 14 may be hydrocracked under hydrogen partial pressures in the range from about 70 bara to about 180 bara, temperatures in the range from about 390° C. to about 460° C., and LHSV in the range from about 0.1 $h^{-1}$ to about 2.0 $h^{-1}$ in the presence of a catalyst. In some embodiments, operating conditions in the hydrocracking reactor system 20 may be similar to those described above for the ebullated bed reactor system 42. In other embodiments, such as where the hydrocracking reactor system 20 includes one or more ebullated bed reactors, the ebullated bed reactors may be operated at higher severity conditions than those in reactor system 42, higher severity referring to a higher temperature, a higher pressure, a lower space velocity or combinations thereof.

The number of reactors used in hydrocracking reactor system 20 may depend on the charge rate, the overall target residue conversion level, and the level of conversion attained in ebullated bed reactor system 42 and fixed bed reactor 12, among other variables. In some embodiments, one or two hydrocracking reactors may be used in hydrocracking reactor system 20. For hydrocracking reactor system 20, the reactor severity may be in the range from about 215,000° F.-Bara-Hr to about 755,000° F.-Bara-Hr.

Following conversion in hydrocracking reactor system 20, the partially converted hydrocarbons may be recovered via flow line 27 as a mixed vapor/liquid effluent and fed to the fractionation system 46 to recover one or more hydrocarbon fractions. As illustrated, fractionation system 46 may be used to recover an offgas 48 containing light hydrocarbon gases and hydrogen sulfide ($H_2S$), a light naphtha fraction 50, a heavy naphtha fraction 52, a kerosene fraction 54, a diesel fraction 56, a light vacuum gas oil fraction 58, a heavy gas oil fraction 60, and a vacuum residuum fraction 62.

Fractionation system 46 may include, for example, a high pressure high temperature (HP/HT) separator to separate the effluent vapor from the effluent liquids. The separated vapor may be routed through gas cooling, purification, and recycle gas compression, or may be first processed through an Integrated Hydroprocessing Reactor System (IHRS), which may include one or more additional hydroconversion reactors, alone or in combination with external distillates and/or distillates generated in the hydrocracking process, and thereafter routed for gas cooling, purification, and compression.

The fractionation system may also include a high pressure medium temperature (HP/MT) separator and a high pressure low temperature (HP/LT) separator. The vapor from the HP/HT separator may cooled by preheating recycle hydrogen gas and feed oil, or by generating high pressure steam prior to entering the HP/MT separator. The vapor from the HP/MT separator may be mixed with wash water to prevent sublimation of ammonium salts and then air cooled. The quantity of wash water is adjusted to limit the concentration of ammonium salts in the effluent water. After air cooling, a three-phase mixture is enters the HP/LT separator which separates the mixture into a vapor, liquid and water phase. The recovered sour water is flashed and routed to battery limits. The vapor is treated to remove hydrogen sulfide ($H_2S$).

The separated liquid from the HP/HT separator may be flashed and routed to an atmospheric distillation system along with other distillate products recovered from the gas cooling and purification section. The atmospheric tower bottoms, such as hydrocarbons having an initial boiling point of at least about 340° C., such as an initial boiling point in the range from about 340° C. to about 427° C., may then be further processed through a vacuum distillation system to recover vacuum distillates.

The atmospheric distillation system may include an atmospheric tower feed furnace to heat the feed. The feed may also be stripped of H2S to reduce the H2S content of the towers bottom to less than 10 wppm. The atmospheric tower may also include an atmospheric reflux drum to condense water and separate hydrocarbon liquids and uncondensed vapor. The condensed hydrocarbon liquid is returned to the atmospheric tower. A sidecut of kerosene may be split into an upper pumparound and a Kerosene Stripper feed. The upper pumparound may reboil a Naphtha Splitter in a Light Ends Recovery Section. Overhead gas from the Kerosene Stripper is returned to the atmospheric tower and bottoms are pumped to off-site battery limits (OSBL) as kerosene product. A sidecut of diesel may be split into a lower pumparound and a Diesel Stripper feed. The lower pumparound may reboil the Naphtha Stabilizer in the Light Ends Recovery Section before returning to the atmospheric tower. The Diesel Stripper overhead is returned to the atmospheric tower and the bottoms pumped to OSBL as diesel product.

The atmospheric bottoms are let down to vacuum conditions and enter the feed flash zone of a vacuum tower of the vacuum distillation system. The feed is separated into vapor and liquid in the vacuum tower flash zone.

The vacuum tower bottoms product, such as hydrocarbons having an initial boiling point of at least about 480° C., such as an initial boiling point in the range from about 480° C. to about 565° C., may then be routed to tankage after cooling, such as by direct heat exchange or direct injection of a portion of the residuum hydrocarbon feed into the vacuum tower bottoms product. A portion of the vacuum tower bottoms product may be returned to the vacuum tower to quench the bottoms liquid. The vacuum tower overhead may be cooled such that the hydrocarbon liquid is separated from water which are pumped to OSBL.

The Light Ends Recovery Section includes a Naphtha Stabilizer which removes the C4 minus material as an overhead for further treating in an absorber. The bottoms from the Naphtha Stabilizer is sent to a Naphtha Splitter to provide a Light and Heavy Naphtha Products.

Catalysts useful in the ebullated bed reactors or hydrocracking reactors may include any catalyst useful in the hydroconversion processes of hydrotreating or hydrocracking a hydrocarbon feedstock. A hydrotreating catalyst, for example, may include any catalyst composition that may be used to catalyze the hydrogenation of hydrocarbon feedstocks to increase its hydrogen content and/or remove heteroatom contaminants. A hydrocracking catalyst, for example, may include any catalyst composition that may be used to catalyze the addition of hydrogen to large or complex hydrocarbon molecules as well as the cracking of the molecules to obtain smaller, lower molecular weight molecules.

Because the organometallic compounds content of the residuum hydrocarbon fraction (residuum) 10 may vary, alternate embodiments of the process shown in FIG. 1 may be utilized. The process flow diagram of FIG. 1 showing an ebullated bed reactor system 42 before a fixed bed reactor 12 may be used when the content of the organometallic compounds in the residuum 10 exceeds from about 75 to about 100 ppm. Makeup catalyst can be continually fed to the ebullated bed reactor system 42 without having to shut down the process. The ebullated bed reactor system 42 may include a demetallization catalyst and the fixed bed reactor may include hydrotreating catalyst.

Figure 2:
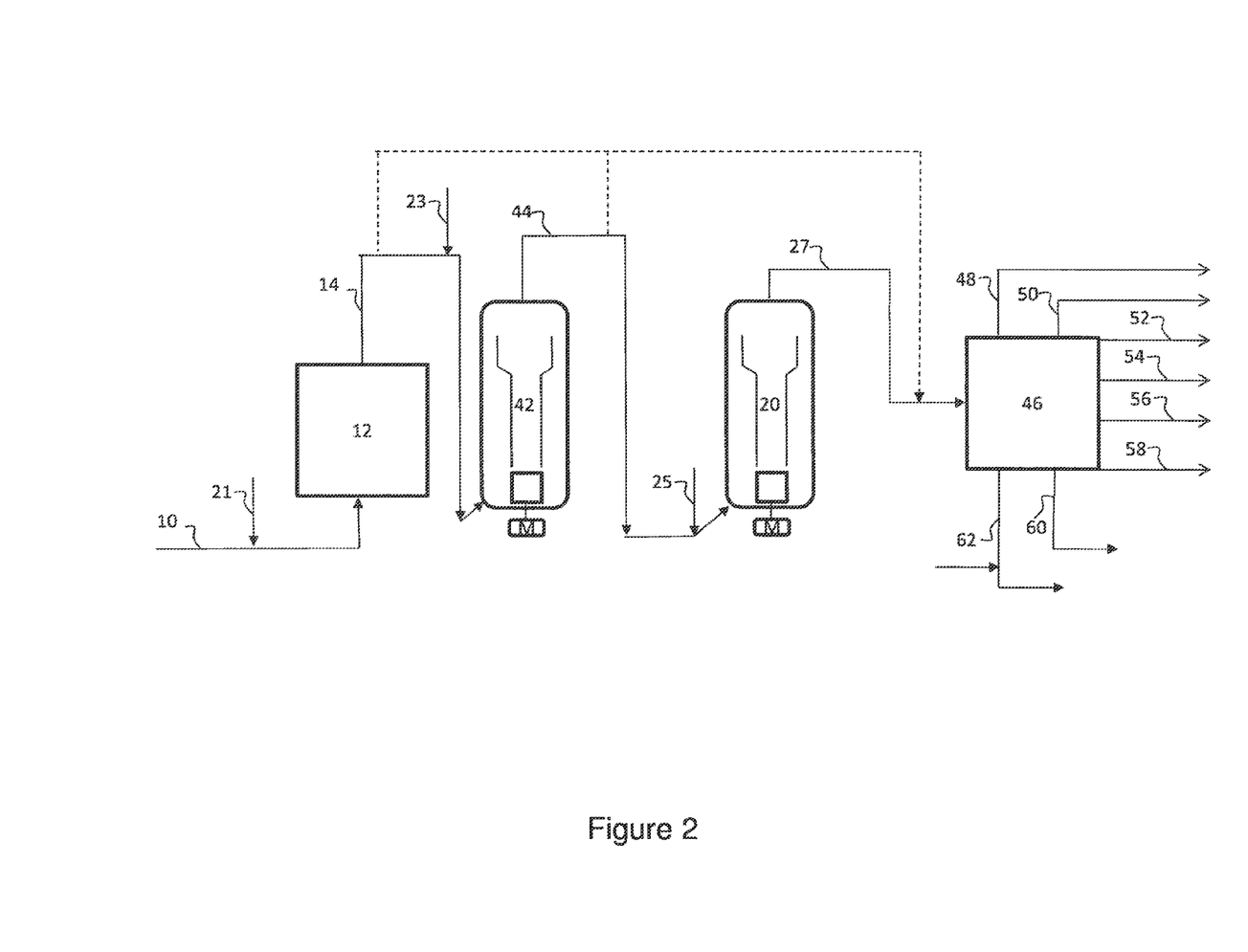
FIG. 2 is a simplified process flow diagram of a process for upgrading residuum hydrocarbon feedstocks according to embodiments disclosed herein.

When the content of the organometallic compounds of residuum hydrocarbon fraction (residuum) 10 ranges from about 50 to about 75 ppm, the process flow diagram of FIG. 2 may be used. In this alternate embodiment, fixed bed reactor 12 may be placed before the ebullated bed reactor system 42. The fixed bed reactor 12 may include hydrodemetallization catalyst. The demetallized and partially desulfurized stream 14 may be fed to the hydrocracking reactor system 20 for further hydrocracking and heteroatom removal at low catalyst makeup rates. The fixed bed reactor 12 may be operated in upflow mode. When the hydrodemetallization catalyst becomes deactivated, the residuum 10 can bypass the fixed bed reactor 12 and enter the ebullated bed reactor system 42. The ebullated bed reactor system 42 will not be shut down and the fixed bed reactor 12 may be unloaded and reloaded with fresh catalyst. The partially converted hydrocarbons 44 will then be combined with hydrogen 25 and fed to the hydrocracking reactor system 20 as described above.

Piping and valving may be used to provide a flexible arrangement of the fixed bed reactor 12 and the ebullated bed reactor system 42, i.e., fixed bed reactor 12 before the ebullated bed reactor system 42 or the ebullated bed reactor system 42 before the fixed bed reactor 12 and the associated downstream equipment. These flexible arrangements afford for switching of residuum hydrocarbon fraction (residuum) 10 feeds while utilizing the same equipment. Streams and equipment with the same reference number across numerous figures may be assumed to be the same.

In some embodiments, the effluents from the hydrocracking reactor system 20, the ebullated bed reactor system 42, or the fixed bed reactor system 12 may be processed prior to entering the fractionation system 46 through an Integrated Hydroprocessing Reactor System (IHRS). The IHRS is an inline fixed-bed hydrotreating system utilizing an upstream high pressure/high temperature vapor/liquid (HP/HT V/L) separator located between the ebullated-bed hydroprocessing reactor and the downstream IHRS. The separator allows for a separation between the unconverted residuum in the liquid effluent of the HP/HT V/L separator and the overhead vapor products boiling below about 1000° F. normal boiling point which may provide a lower cost route for further hydrotreating or hydrocracking of the gas oils, diesel and naphtha fractions formed by cracking of residuum in the upstream ebullated bed reactor.

Figure 3:
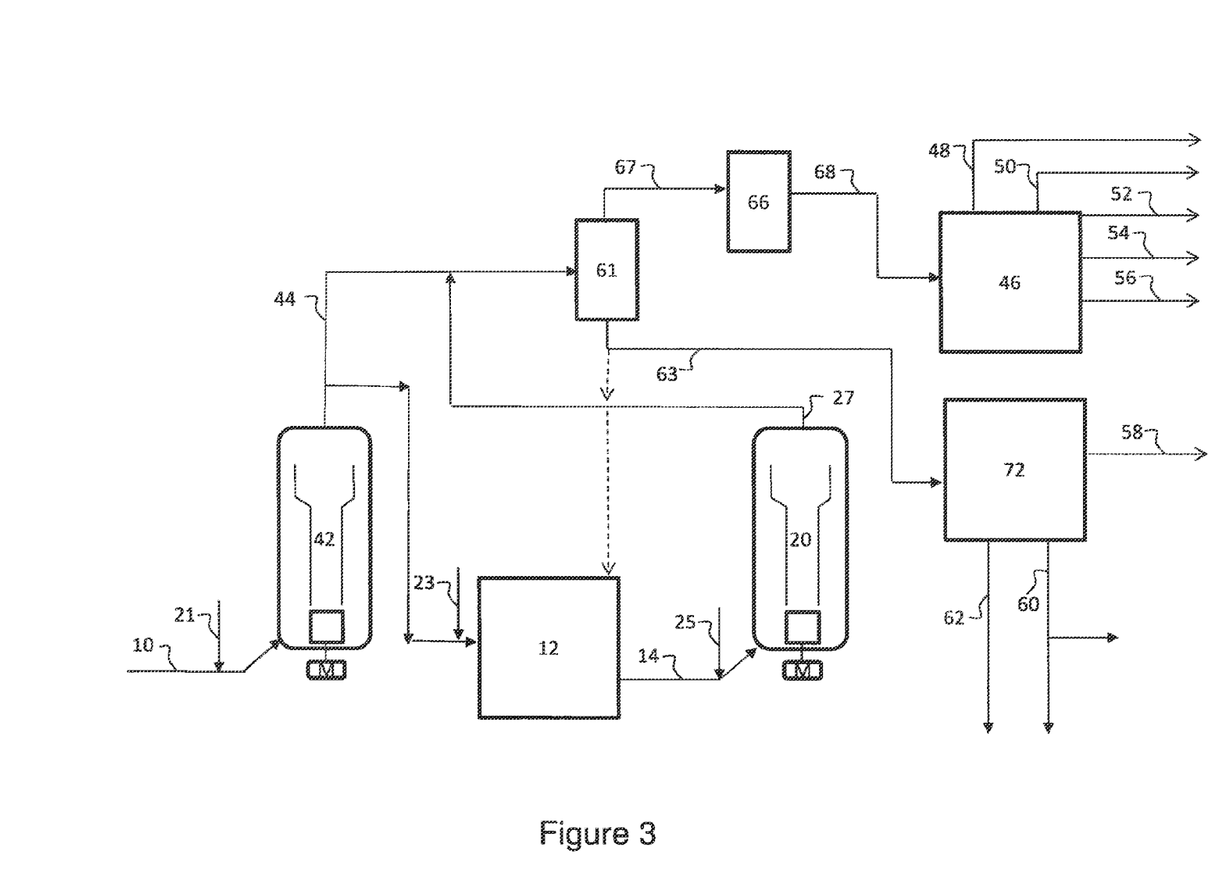
FIG. 3 is a simplified process flow diagram of a process for an integrated hydroprocessing reactor system to be used with a process for upgrading residuum hydrocarbon feedstocks according to embodiments disclosed herein.
Figure 4:
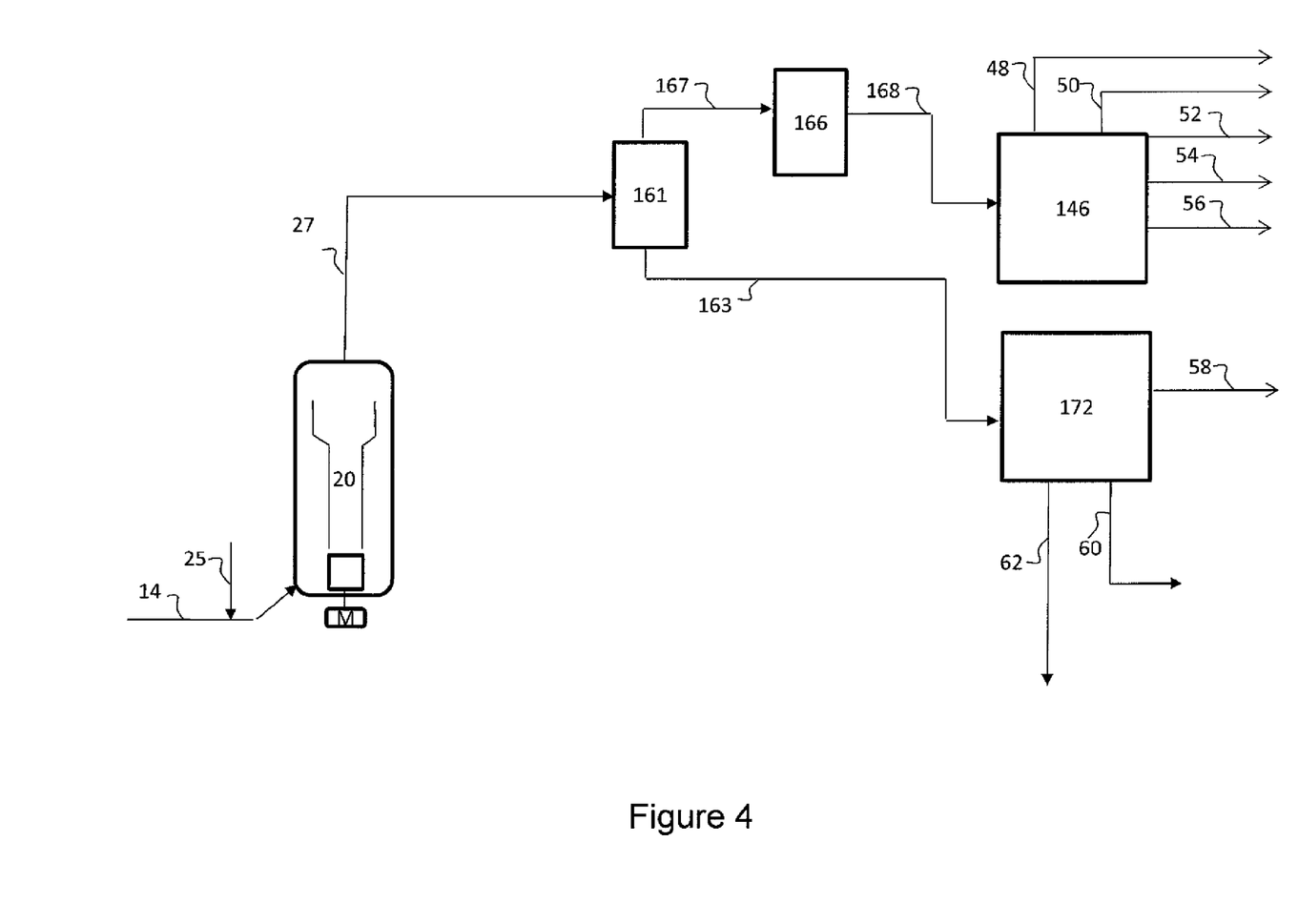
FIG. 4 is a simplified process flow diagram of a process for an integrated hydroprocessing reactor system to be used with a process for upgrading residuum hydrocarbon feedstocks according to embodiments disclosed herein.

FIGS. 3 and 4 illustrate two embodiments for the IMS and are described below, however other embodiments will be obvious to those skilled in the art as being possible. FIG. 3 illustrates an embodiment where the MRS is installed downstream of the blended stream derived by mixing the partially converted hydrocarbons recovered via flow line 44 from ebullated bed reactor system 42 and the partially converted hydrocarbons recovered via flow line 27 from the hydrocracking reactor system 20. FIG. 4 illustrates an embodiment where the IHRS is installed downstream of the ebullated bed hydroprocessing reactor 20.

As shown in FIG. 3, the effluent streams 44 and 27 from ebullated bed hydroprocessing reactor 42 and the hydrocracking reactor system 20, respectively, may be cooled in a heat exchanger (not shown) and fed to a HP/HT V/L separator 61 where a vapor stream including the light products and distillates boiling below about 1000° F. normal boiling point and a liquid stream including unconverted residuum may be separated and processed separately in downstream equipment. A vapor stream 67 may be fed to a fixed-bed hydroprocessing reactor 66 to carry out hydrotreating, hydrocracking or a combination thereof. An effluent stream 68 from the IHRS fixed-bed reactor system 66 is fed to the fractionation system 46 which recovers an offgas stream 48, light hydrotreated or hydrocracked naphtha stream 50, heavy hydrotreated or hydrocracked naphtha stream 52, hydrotreated or hydrocracked kerosene stream 54, hydrotreated or hydrocracked diesel stream 56, as described above. The liquid stream 63 may be cooled in a heat exchanger (not shown) and depressurized in a pressure letdown system (not shown) before being fed to a vacuum fractionation system 72 which recovers a light hydrotreated or hydrocracked VGO stream 58, a heavy hydrotreated or hydrocracked VGO stream 60 and an unconverted vacuum residuum stream 62. In some embodiments, the vacuum tower bottoms product stream, such as hydrocarbons having an initial boiling point of at least about 480° C., such as an initial boiling point in the range from about 480° C. to about 565° C., may be routed to tankage after cooling, such as by direct heat exchange or direct injection of a portion of the residuum hydrocarbon feed into the vacuum tower bottoms product.

As shown in FIG. 4, the effluent stream 27 from the ebullated bed reactor system 20 may be cooled in a heat exchanger (not shown) and fed to a HP/HT V/L separator 161 where a vapor stream including the light products and distillates boiling below about 1000° F. normal boiling point and a liquid stream including unconverted residuum may be separated and processed separately in downstream equipment. A vapor stream 167 is fed to a fixed-bed hydroprocessing reactor 166 to carry out hydrotreating, hydrocracking or a combination thereof. An effluent stream 168 from the IHRS fixed-bed reactor system 166 may be fed to an atmospheric fractionation system 146 which recovers an offgas stream 26, light hydrotreated or hydrocracked naphtha stream 28, heavy hydrotreated or hydrocracked naphtha stream 30, hydrotreated or hydrocracked kerosene stream 32, hydrotreated or hydrocracked diesel stream 34. A liquid stream 163 is cooled in a heat exchanger (not shown) and depressurized in a pressure letdown system (not shown) and may be fed to a vacuum fractionation system 172 which recovers a light hydrotreated or hydrocracked VGO stream 36, a heavy hydrotreated or hydrocracked VGO stream 38 and an unconverted vacuum residuum stream 40. In some embodiments, the vacuum tower bottoms product stream, such as hydrocarbons having an initial boiling point of at least about 480° C., such as an initial boiling point in the range from about 480° C. to about 565° C., may then be routed to tankage after cooling, such as by direct heat exchange or direct injection of a portion of the residuum hydrocarbon feed into the vacuum tower bottoms product.

Hydroconversion catalyst compositions for use in the hydroconversion process according to embodiments disclosed herein are well known to those skilled in the art and several are commercially available from W.R. Grace & Co., Criterion Catalysts & Technologies, and Albemarle, among others. Suitable hydroconversion catalysts may include one or more elements selected from Groups 4-12 of the Periodic Table of the Elements. In some embodiments, hydroconversion catalysts according to embodiments disclosed herein may comprise, consist of or consist essentially of one or more of nickel, cobalt, tungsten, molybdenum and combinations thereof, either unsupported or supported on a porous substrate such as silica, alumina, titania, or combinations thereof. As supplied from a manufacturer or as resulting from a regeneration process, the hydroconversion catalysts may be in the form of metal oxides, for example. In some embodiments, the hydroconversion catalysts may be pre-sulfided and/or pre-conditioned prior to introduction to the hydrocracking reactor(s).

Distillate hydrotreating catalysts that may be useful include catalyst selected from those elements known to provide catalytic hydrogenation activity. At least one metal component selected from Group 8-10 elements and/or from Group 6 elements is generally chosen. Group 6 elements may include chromium, molybdenum and tungsten. Group 8-10 elements may include iron, cobalt, nickel, ruthenium, rhodium, palladium, osmium, iridium and platinum. The amount(s) of hydrogenation component(s) in the catalyst suitably range from about 0.5% to about 10% by weight of Group 8-10 metal component(s) and from about 5% to about 25% by weight of Group 6 metal component(s), calculated as metal oxide(s) per 100 parts by weight of total catalyst, where the percentages by weight are based on the weight of the catalyst before sulfiding. The hydrogenation components in the catalyst may be in the oxidic and/or the sulphidic form. If a combination of at least a Group 6 and a Group 8 metal component is present as (mixed) oxides, it will be subjected to a sulfiding treatment prior to proper use in hydrocracking. In some embodiments, the catalyst comprises one or more components of nickel and/or cobalt and one or more components of molybdenum and/or tungsten or one or more components of platinum and/or palladium. Catalysts containing nickel and molybdenum, nickel and tungsten, platinum and/or palladium are useful.

Residue hydrotreating catalyst that may be useful include catalysts generally composed of a hydrogenation component, selected from Group 6 elements (such as molybdenum and/or tungsten) and Group 8-10 elements (such as cobalt and/or nickel), or a mixture thereof, which may be supported on an alumina support. Phosphorous (Group 15) oxide is optionally present as an active ingredient. A typical catalyst may contain from 3 to 35 wt % hydrogenation components, with an alumina binder. The catalyst pellets may range in size from 1/32 inch to 1/8 inch, and may be of a spherical, extruded, trilobate or quadrilobate shape. In some embodiments, the feed passing through the catalyst zone contacts first a catalyst preselected for metals removal, though some sulfur, nitrogen and aromatics removal may also occur. Subsequent catalyst layers may be used for sulfur and nitrogen removal, though they would also be expected to catalyze the removal of metals and/or cracking reactions. Catalyst layer(s) for demetallization, when present, may comprise catalyst(s) having an average pore size ranging from 125 to 225 Angstroms and a pore volume ranging from 0.5-1.1 $cm^3/g$. Catalyst layer(s) for denitrogenation/desulfurization may comprise catalyst(s) having an average pore size ranging from 100 to 190 Angstroms with a pore volume of 0.5-1.1 $cm^3/g$. U.S. Pat. No. 4,990,243 describes a hydrotreating catalyst having a pore size of at least about 60 Angstroms, and preferably from about 75 Angstroms to about 120 Angstroms. A demetallization catalyst useful for the present process is described, for example, in U.S. Pat. No. 4,976,848, the entire disclosure of which is incorporated herein by reference for all purposes. Likewise, catalysts useful for desulfurization of heavy streams are described, for example, in U.S. Pat. Nos. 5,215,955 and 5,177,047, the entire disclosures of which are incorporated herein by reference for all purposes. Catalysts useful for desulfurization of middle distillate, vacuum gas oil streams and naphtha streams are described, for example, in U.S. Pat. No. 4,990,243, the entire disclosures of which are incorporated herein by reference for all purposes.

Useful residue hydrotreating catalysts include catalysts having a porous refractory base made up of alumina, silica, phosphorous, or various combinations of these. One or more types of catalysts may be used as residue hydrotreating catalyst, and where two or more catalysts are used, the catalysts may be present in the reactor zone as layers. The catalysts in the lower layer(s) may have good demetallization activity. The catalysts may also have hydrogenation and desulfurization activity, and it may be advantageous to use large pore size catalysts to maximize the removal of metals. Catalysts having these characteristics are not optimal for the removal of Conradson Carbon Residue and sulfur. The average pore size for catalyst in the lower layer or layers will usually be at least 60 Angstroms and in many cases will be considerably larger. The catalyst may contain a metal or combination of metals such as nickel, molybdenum, or cobalt. Catalysts useful in the lower layer or layers are described in U.S. Pat. Nos. 5,071,805 5,215,955, and 5,472,928. For example, those catalysts as described in U.S. Pat. No. 5,472,928 and having at least 20% of the pores in the range of 130 to 170 Angstroms, based on the nitrogen method, may be useful in the lower catalysts layer(s). The catalysts present in the upper layer or layers of the catalyst zone should have greater hydrogenation activity as compared to catalysts in the lower layer or layers. Consequently catalysts useful in the upper layer or layers may be characterized by smaller pore sizes and greater Conradson Carbon Residue removal, denitrogenation and desulfurization activity. Typically, the catalysts will contain metals such as, for example, nickel, tungsten, and molybdenum to enhance the hydrogenation activity. For example, those catalysts as described in U.S. Pat. No. 5,472,928 and having at least 30% of the pores in the range of 95 to 135 Angstroms, based on the nitrogen method, may be useful in the upper catalysts layers. The catalysts may be shaped catalysts or spherical catalysts. In addition, dense, less friable catalysts may be used in the upflow fixed catalyst zones to minimize breakage of the catalyst particles and the entrainment of particulates in the product recovered from the reactor.

One skilled in the art will recognize that the various catalyst layers may not be made up of only a single catalyst, but may be composed of an intermixture of different catalysts to achieve the optimal level of metals or Conradson Carbon Residue removal and desulfurization for that layer. Although some hydrogenation will occur in the lower portion of the zone, the removal of Conradson Carbon Residue, nitrogen, and sulfur may take place primarily in the upper layer or layers. Obviously additional metals removal also will take place. The specific catalyst or catalyst mixture selected for each layer, the number of layers in the zone, the proportional volume in the bed of each layer, and the specific hydrotreating conditions selected will depend on the feedstock being processed by the unit, the desired product to be recovered, as well as commercial considerations such as cost of the catalyst. All of these parameters are within the skill of a person engaged in the petroleum refining industry and should not need further elaboration here.

As described above, embodiments disclosed herein effectively processes vacuum residue and intermediate streams through multiple hydrocracking reactors, each operating at different severities and processing different feed compositions with a SDA located within the process, extending the residue conversion limits above those which can be attained by residue hydrocracking alone. Further, the higher conversions may be attained using less catalytic reactor volume as compared to other schemes proposed to achieve similar conversions. As a result, embodiments disclosed herein may provide comparable or higher conversions but requiring a lower capital investment requirement. Further, embodiments disclosed herein may be used to produce a fuel oil having less than 1 wt % sulfur from a high sulfur containing residue feed while maximizing overall conversion.

The overall processing schemes disclosed herein may be performed using low reactor volumes while still achieving high conversions. Likewise, other resulting advantages may include: reduced catalyst consumption rates due to rejecting metals in the asphalt from the SDA unit; reduced capital investment; and elimination or significant reduction in the need for injection of slurry oil upstream of the ebullated bed reactors, among other advantages.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for upgrading residuum hydrocarbons, the process comprising:
   contacting a residuum hydrocarbon fraction and hydrogen with a first hydroconversion catalyst in a first ebullated bed hydroconversion reactor system;
   recovering a first effluent from the first ebullated bed hydroconversion reactor system;
   contacting a first portion of the first effluent and hydrogen with a second hydroconversion catalyst in a second hydroconversion reactor system;
   recovering a second effluent from the second hydroconversion reactor system;
   contacting the second effluent and hydrogen with a third hydroconversion catalyst in a second ebullated bed hydroconversion reactor system;
   recovering a third effluent from the second ebullated bed hydroconversion reactor system; and
   fractionating the third effluent from the second ebullated bed hydroconversion reactor system to recover one or more hydrocarbon fractions,
   wherein a second portion of the first effluent and the third effluent is fed to a common fractionation system.

2. The process of claim 1, wherein the second hydroconversion reactor system comprises a fixed bed reactor.

3. The process of claim 1, further comprising recycling a vacuum residuum hydrocarbon fraction to at least one of the first ebullated bed hydroconversion reactor system, the second hydroconversion reactor system, and the second ebullated bed hydroconversion reactor system.

4. The process of claim 1, further comprising recycling a vacuum gas oil hydrocarbon fraction to at least one of the first ebullated bed hydroconversion reactor system, the second hydroconversion reactor system, and the second ebullated bed hydroconversion reactor system.

5. The process of claim 1, wherein the residuum hydrocarbon fraction comprises at least one of petroleum atmospheric or vacuum residua, deasphalted oils, deasphalter pitch, hydrocracked atmospheric tower or vacuum tower bottom, straight run vacuum gas oil, hydrocracked vacuum gas oil, fluid catalytically cracked (FCC) slurry oils, vacuum gas oil from an ebullated bed process, shale-derived oils, coal-derived oils, bioderived crude oils, tar sands bitumen, tall oils, black oils.

6. The process of claim 1, wherein the contacting in the first ebullated bed hydroconversion reactor system comprises selecting operating conditions sufficient to result in a hydrocarbon conversion in the range from about 25 wt % to about 35 wt % and metals removal in the range from about 50 wt % to about 80 wt %.

7. The process of claim 1, wherein the contacting in the second hydroconversion reactor system comprises selecting operating conditions sufficient to result in a hydrocarbon conversion in the range from about 40 wt % to about 55 wt %, a desulfurization/denitrogenation rate in the range from about 70 to about 85%, and Conradson Carbon Residue removal is in the range from about 60 wt % to about 70 wt %.

8. The process of claim 1, wherein the contacting in the second ebullated bed hydroconversion reactor system comprises selecting operating conditions sufficient to result in a hydrocarbon conversion in the range from about 30 wt % to about 75 wt % and a desulfurization/denitrogenation rate in the range from about 85 to about 95%.

9. The process of claim 1, wherein a fuel oil produced via the fractionating the second ebullated bed hydroconversion reactor system effluent has a sulfur content of about 1.0 wt % or less.

10. The process of claim 1, wherein an overall conversion of the residuum hydrocarbon fraction is in the range from about 70 wt % to about 80 wt %.

11. The process of claim 1, wherein the temperature in the second ebullated-bed hydroconversion system is greater than the temperature in the first ebullated-bed hydroconversion system.

12. A system for upgrading residuum hydrocarbons, the system comprising:
   a first ebullated bed hydroconversion reactor system for contacting a residuum hydrocarbon fraction and hydrogen with a first hydroconversion catalyst to produce a first effluent;
   a second hydroconversion reactor system for contacting a first portion of the first effluent and hydrogen with a second hydroconversion catalyst to produce a second effluent;
   a second ebullated bed hydroconversion reactor system for contacting the second effluent and hydrogen with a third hydroconversion catalyst to produce a third effluent and
   a fractionation unit to fractionate the third effluent and a second portion of the first effluent to recover one or more hydrocarbon fractions and a vacuum residuum fraction.

13. The system of claim 12, wherein the second hydroconversion reactor system includes a fixed bed hydroconversion reactor system.

14. A process for upgrading residuum hydrocarbons, the process comprising:

contacting a residuum hydrocarbon fraction and hydrogen with a first hydroconversion catalyst in a first ebullated bed hydroconversion reactor system;

recovering a first effluent from the first ebullated bed hydroconversion reactor system;

separating a first portion of the first effluent into a liquid product and a vapor product;

contacting a portion of the liquid product and hydrogen with a second hydroconversion catalyst in a second hydroconversion reactor system;

recovering a second effluent from the second hydroconversion reactor system;

contacting the second effluent and hydrogen with a third hydroconversion catalyst in a third hydroconversion reactor system;

recovering a third effluent from the third hydroconversion reactor system;

combining the first effluent and the third effluent to form a combined feed;

feeding the combined feed to a separator to produce a vapor fraction and a liquid fraction;

fractionating the liquid fraction to recover the vacuum residuum fraction in a first fractionation system;

contacting the vapor fraction with a fourth hydroconversion catalyst in a fourth hydroconversion reactor system;

recovering a fourth effluent from the fourth hydroconversion reactor system;

fractionating the fourth effluent to recover one or more hydrocarbon fractions in a second fractionation system.

15. A system for upgrading residuum hydrocarbons, the system comprising:

a first ebullated bed hydroconversion reactor system for contacting a residuum hydrocarbon fraction and hydrogen with a first hydroconversion catalyst to produce a first effluent;

a separator for separating the first effluent into a liquid product and a vapor product;

a second hydroconversion reactor system for contacting the liquid product and hydrogen with a second hydroconversion catalyst to produce a second effluent;

a second ebullated bed hydroconversion reactor system for contacting the second effluent and hydrogen with a third hydroconversion catalyst to produce a third effluent; and the separator further separating a combined fraction of the first effluent and the third effluent to recover a liquid fraction and a vapor fraction;

a first fractionation unit to fractionate the liquid to recover the vacuum residuum fraction;

a fourth hydroconversion reactor system for contacting the vapor fraction with a fourth hydroconversion catalyst to produce a fourth effluent; and a second fractionation unit to fractionate the fourth effluent to recover one or more hydrocarbon fractions.

16. A process for upgrading residuum hydrocarbons, the process comprising:

contacting a residuum hydrocarbon fraction and hydrogen with a first hydroconversion catalyst in a first hydroconversion reactor system;

recovering a first effluent from the first hydroconversion reactor system;

contacting a first portion of the first effluent and hydrogen with a second hydroconversion catalyst in a first ebullated bed hydroconversion reactor system;

recovering a second effluent from the first ebullated bed hydroconversion reactor system;

contacting a first portion of the second effluent and hydrogen with a third hydroconversion catalyst in a second ebullated bed hydroconversion reactor system;

recovering a third effluent from the second ebullated bed hydroconversion reactor system; and fractionating the third effluent from the second ebullated bed hydroconversion reactor system to recover one or more hydrocarbon fractions, wherein a second portion of the first effluent, a second portion of the second effluent and the third effluent is fed to a common fractionation system.

* * * * *